United States Patent
Barger et al.

(10) Patent No.: US 7,324,864 B2
(45) Date of Patent: Jan. 29, 2008

(54) APPARATUS AND METHOD FOR MEASURING FORCES IMPARTED ON VALVE ASSEMBLIES OF METERED DOSE DELIVERY CONTAINERS DURING MANUFACTURE THEREOF

(75) Inventors: Lee A. Barger, Durham, NC (US); David Brian Moody, Durham, NC (US); Donald Devereaux Munn, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 598 days.

(21) Appl. No.: 10/480,729

(22) PCT Filed: Jun. 12, 2002

(86) PCT No.: PCT/US02/18954

§ 371 (c)(1),
(2), (4) Date: Dec. 12, 2003

(87) PCT Pub. No.: WO02/103318

PCT Pub. Date: Dec. 27, 2002

(65) Prior Publication Data

US 2004/0148042 A1    Jul. 29, 2004

Related U.S. Application Data

(60) Provisional application No. 60/298,626, filed on Jun. 15, 2001.

(51) Int. Cl.
| | |
|---|---|
| *G06F 19/00* | (2006.01) |
| *G01M 7/00* | (2006.01) |
| *G01M 3/00* | (2006.01) |
| *G01M 3/30* | (2006.01) |
| *G01M 3/02* | (2006.01) |

(52) U.S. Cl. .................. 700/117; 700/95; 700/108; 700/145; 700/165; 73/12.01; 73/12.07; 73/37; 73/52

(58) Field of Classification Search ............ 700/301, 700/165, 206, 95, 108, 117, 145; 702/33, 702/41; 73/12.01, 12.07, 37, 52
See application file for complete search history.

(56) References Cited

U.S. PATENT DOCUMENTS

| | | | | |
|---|---|---|---|---|
| 4,047,613 A | * | 9/1977 | Wright ...................... 209/558 |
| 4,315,427 A | * | 2/1982 | Leiter et al. .................. 73/52 |
| 4,337,644 A | * | 7/1982 | Leiter ........................... 73/52 |

(Continued)

FOREIGN PATENT DOCUMENTS

FR    2 800 652    5/2001

*Primary Examiner*—Ronald D Hartman, Jr.
(74) *Attorney, Agent, or Firm*—Alice P. Bradney

(57) ABSTRACT

An axial force measurement apparatus (40) comprises a head member (42) adapted for receiving force imparted by an external force-applying source, and a transducer (44) such as a load cell for measuring the amount of force applied to the head member (42). Electronic circuitry (61) for receiving, processing, storing and/or sending electrical information generated by the transducer is provided either externally to the measurement apparatus (40), or is integrated with the apparatus (40). The apparatus (40) can be used to calibrate the valve crimping station (75) and/or the test firing station (125) of a metered dose delivery canister production line. The apparatus (40) is designed to emulate an actual canister (12).

27 Claims, 15 Drawing Sheets

U.S. PATENT DOCUMENTS

| | | | |
|---|---|---|---|
| 4,459,843 A * | 7/1984 | Durham | 73/37 |
| 4,511,044 A * | 4/1985 | Connor et al. | 209/522 |
| 4,706,494 A * | 11/1987 | Creed et al. | 73/49.3 |
| 4,771,630 A * | 9/1988 | Croce et al. | 73/49.3 |
| 4,899,574 A * | 2/1990 | Potteiger | 73/52 |
| 5,101,651 A | 4/1992 | Yeomans | |
| 5,168,736 A | 12/1992 | Enneper et al. | |
| 5,197,186 A | 3/1993 | Strong et al. | |
| 5,209,483 A * | 5/1993 | Gedney et al. | 473/223 |
| 5,261,538 A * | 11/1993 | Evans et al. | 209/2 |
| 5,271,254 A | 12/1993 | Gloe et al. | |
| 5,299,463 A | 4/1994 | Gross | |
| 5,307,685 A * | 5/1994 | Bloome et al. | 73/756 |
| 5,829,289 A * | 11/1998 | Fisher et al. | 72/19.9 |
| 5,937,505 A | 8/1999 | Strong et al. | |
| 6,067,828 A | 5/2000 | Bucher et al. | |
| 6,161,407 A | 12/2000 | Meisser | |
| 6,212,924 B1 * | 4/2001 | Meisser | 72/21.4 |
| 6,367,312 B1 * | 4/2002 | Yamagishi et al. | 73/49.2 |
| 6,382,008 B1 | 5/2002 | Jaubert | |
| 6,393,900 B1 * | 5/2002 | Buckner et al. | 73/61.56 |
| 6,415,526 B1 * | 7/2002 | Buckner et al. | 33/833 |
| 6,418,769 B1 | 7/2002 | Schreiner | |
| 6,502,320 B2 * | 1/2003 | Buckner et al. | 33/286 |
| 6,505,494 B1 * | 1/2003 | Wollermann | 73/1.15 |
| 2002/0152628 A1 * | 10/2002 | Buckner et al. | 33/833 |
| 2003/0047005 A1 * | 3/2003 | Stalnaker et al. | 73/818 |
| 2004/0134257 A1 * | 7/2004 | Fletcher et al. | 73/37 |
| 2004/0231667 A1 * | 11/2004 | Horton et al. | 128/202.13 |
| 2005/0016527 A1 * | 1/2005 | Barger et al. | 128/200.23 |

* cited by examiner

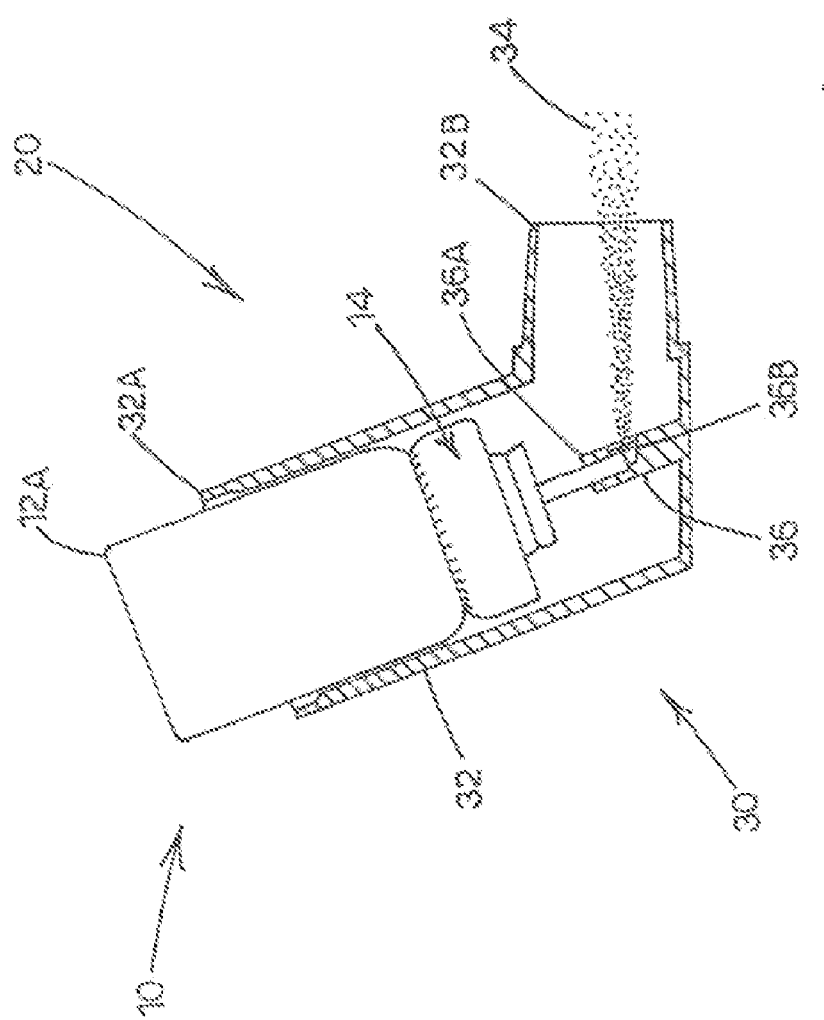

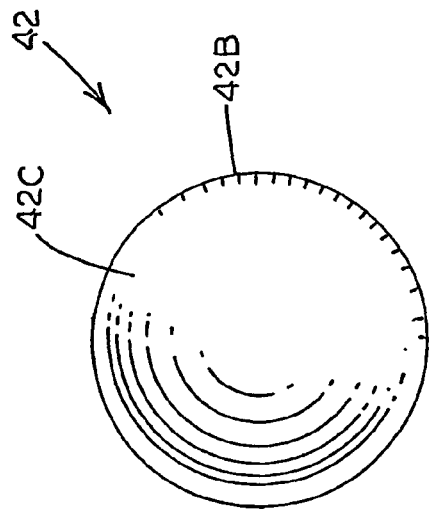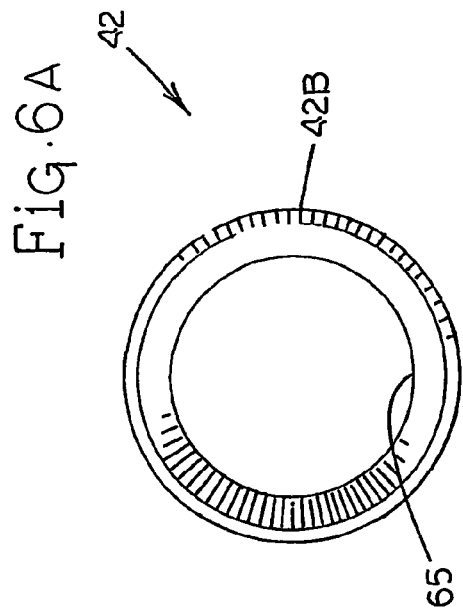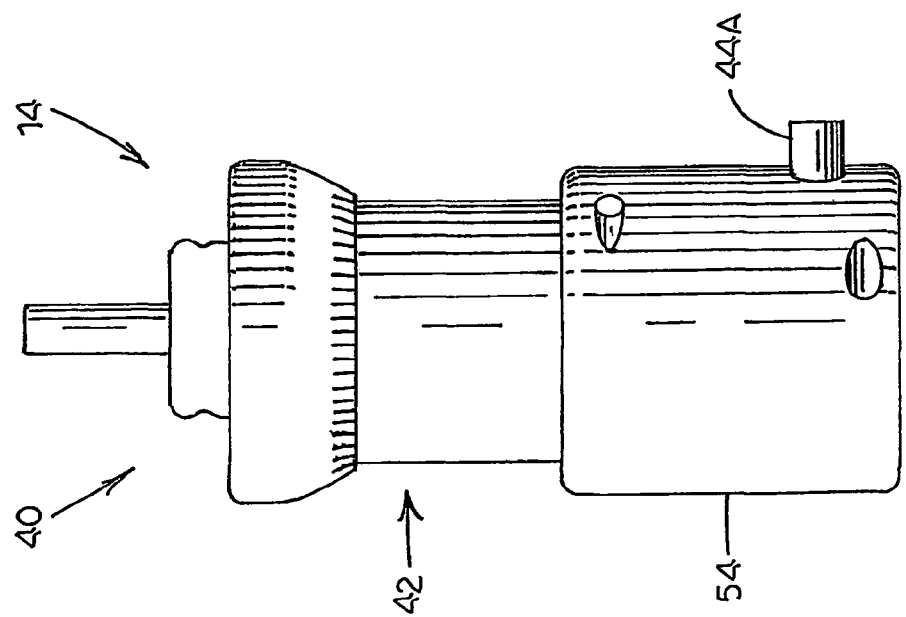

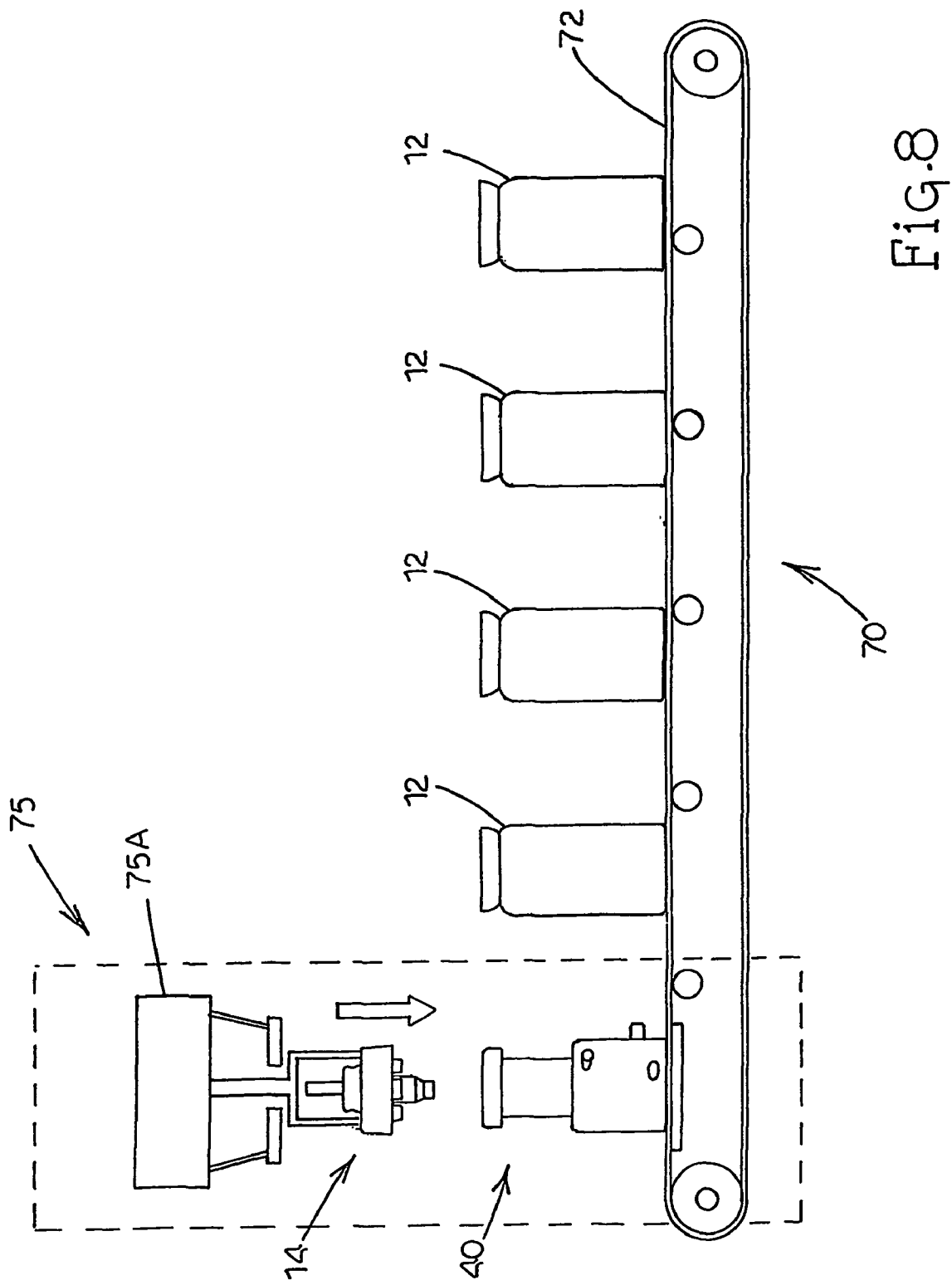

Fig·10

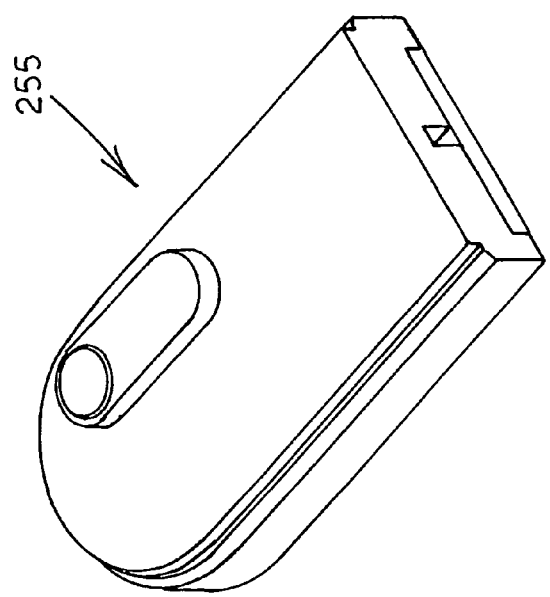
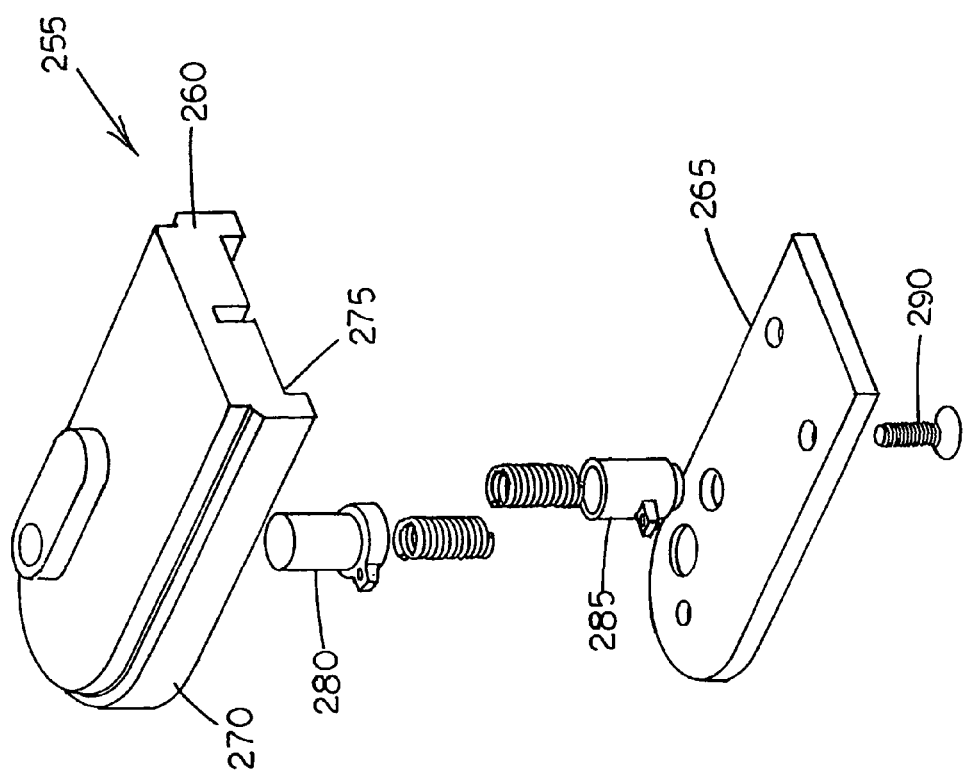

APPARATUS AND METHOD FOR MEASURING FORCES IMPARTED ON VALVE ASSEMBLIES OF METERED DOSE DELIVERY CONTAINERS DURING MANUFACTURE THEREOF

CROSS-REFERENCE TO RELATED APPLICATIONS

This present application is filed under 35 U.S.C. § 371 as the United States National Phase Application of International Application No. PCT/US02/18954 filed Jun. 12, 2002 and claims priority to Provisional Application No. 60/298,626 filed Jun. 15, 2001, the disclosure of which are incorporated herein by reference in their entirety.

TECHNICAL FIELD

The present invention is generally directed to the manufacturing of sealed containers equipped with valves, such as those employed in metered dose delivery units, and the calibration of production equipment utilized in the manufacture of such containers. More particularly, the present invention is directed to testing the integrity of the seal provided by the valves of such containers, through the testing of the crimp force and/or the actuating force imparted on the containers or their valve assemblies, especially propellant-charged canisters containing therapeutically-effective substances for delivery to patients in metered doses.

DISCLOSURE OF THE INVENTION

The present invention disclosed herein results from an acknowledgment that in order for the valve cap to be crimped onto the canister properly, thus ensuring the integrity of the seal, the crimping force imparted on the valve cap by the crimping equipment must accurately fall within a predetermined range during the crimping process. In the present invention, it has now been found that accurately applied crimping force, and thus a seal of acceptable quality, can be indicated by directly measuring the force exerted on a canister in a manner which provides a more reproducible and less subjective means for determining proper crimping equipment setup.

The present invention also results from an acknowledgment that in order for a valve-equipped canister to be test-fired accurately, the actuating force applied by test firing equipment must likewise accurately fall within an acceptable range during the test firing process. In the present invention, it has now been found that test firing equipment can be properly and easily calibrated through the use of embodiments disclosed herein.

The measuring devices provided by the present invention include certain interchangeable parts so as to render the devices compatible with a number of differently sized valve-equipped canisters without undue change-out efforts.

According to one embodiment of the present invention, an apparatus comprises a main body member, a head member, and a transducer. The head member is attached to the main body member, and includes an impact surface adapted for contact with a force. The transducer is in communication with the head member, and is adapted to receive force imparted to the head member.

According to another embodiment of the present invention, an axial force measurement apparatus comprises a head member and an axial force transducer. The head member is coaxially disposed about a longitudinal axis of the measurement apparatus. The head member includes a flanged portion extending radially outwardly from the longitudinal axis, such that the head member presents an outer profile adapted to securably receive a valve assembly on the head member during a valve assembly crimping process. The transducer is coaxially disposed about the longitudinal axis in mechanical communication with the head member. The transducer is adapted to receive an axial force imparted to the head member generally along the longitudinal axis and transferred from the head member to the transducer, and is adapted to produce an electrical output signal indicative of a magnitude of the axial force transferred to the transducer.

According to still another embodiment of the present invention, an axial force measurement apparatus comprises a head member, an axial force transducer, and electronic circuitry. The electronic circuitry is disposed remotely in relation to the transducer and communicates with the transducer through an electrical conduit. The electronic circuitry is adapted to receive the output signal produced by the transducer.

According to yet another embodiment of the present invention, the axial force measurement apparatus includes a housing containing the electronic circuitry.

According to a further embodiment of the present invention, the axial force measurement apparatus includes at least one electrical contact communicating with the electronic circuitry. The contact is adapted to enable communication between the electronic circuitry and an external computer device disposed remotely in relation to the housing of the apparatus.

According to an additional aspect of the present invention, a method is provided for measuring the axial force applied by a machine element. In the method, an axial force measurement apparatus is provided. The apparatus includes a head member coaxially disposed about a longitudinal axis and an axial force transducer mechanically communicating with the head member. A machine element is caused to apply a force having an axially-oriented force component to the head member, wherein the axially-oriented force component is translated from the head member to the transducer. The transducer produces an electrical output signal indicative of the axially-oriented force component translated to the transducer during application of the force to the head member.

According to a still further embodiment of the present invention, a system is provided for determining whether a valve assembly crimping station, such as utilized on a metered dose inhaler unit production line, is properly calibrated. The system comprises a valve assembly crimping station, an axial force measurement device adapted for operative alignment with the crimping station, and electronic circuitry communicating with the transducer. The electronic circuitry is adapted to receive the output signal produced by the transducer.

According to a yet further embodiment of the present invention, a system is provided for determining whether a metered dose delivery device test firing station, such as utilized on a metered dose inhaler unit production line, is properly calibrated. The system comprises a test firing station adapted to actuate a valve assembly, and an axial force measurement device adapted for operative alignment with the test firing station. The measurement device includes a head member, a valve assembly installed on the head member around an outer profile of the head member, an axial force transducer adapted to receive an axial force imparted to the valve assembly by the test firing station and to produce an electrical output signal indicative of a magnitude of the axial force transferred to the transducer, and electronic circuitry communicating with the transducer and adapted to receive the output signal produced by the transducer.

It is therefore an object of the present invention to provide an apparatus and method for measuring the crimp force imparted to a canister during installation of a valve assembly thereon.

It is another object of the present invention to provide an apparatus and method for measuring the actuating force imparted to the valve assembly of a canister during a test-firing procedure of the valve assembly.

It is a further object of the present invention to provide a portable apparatus for measuring the forces imparted to a canister during valve assembly installation and/or test firing processes, which apparatus can be utilized directly on the production line if desired.

It is a still further object of the present invention to provide an apparatus for measuring axial force imparted to a canister or its valve assembly which emulates an actual canister during production.

Some of the objects of the invention having been stated hereinabove, other objects will be evident as the description proceeds, when taken in connection with the accompanying drawings as best described hereinbelow.

BACKGROUND

Many types of medicines are provided in fluid form, such as a solution or suspension of particles in a propellant or emulsion, and are adapted for oral or nasal inhalation by a patient. As one example, a canister might contain asthma or nasal medicine.

Appropriate medicaments may thus might include, for example, analgesics, e.g., codeine, dihydromorphine, ergotamine, fentanyl or morphine; anginal preparations, e.g., diltiazem; antiallergics, e.g., cromoglycate, ketotifen or nedocromil; antuinfectives e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (−)-4-amino-3,5-dichloro-a-[[[6-[2-(2-pyridinyl)ethoxy] hexyl]methyl] benzenemethanol; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant.

Preferred medicaments are selected from albuterol, salmeterol, fluticasone propionate and beclometasone dippropionate and salts or sovates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an antiinflammatory steroid such as a beclomethasone ester (e.g., the dipropionate) or a fluticasone ester (e.g., the propionate).

During a typical manufacturing process, the canister, which is initially open-topped, is sealed with a top or cap that includes a metering valve. The typical metering valve is actuated by a spring-loaded, hollow valve stem through which a metered or controlled, substantially repeatable dose of medicament is delivered out from the interior of the canister. The seal is effected by crimping the valve cap onto the neck of the canister. The canister is then, many times, charged through the valve stem with an aerosol or other propellant such as $CO_2$, CFC 11, CFC 12, P134A or P227 or combinations thereof, so that the medicament is aerosolized upon delivery out from the canister.

In order to deliver medicine to the patient with suitable efficacy, the canister preferably operates in conjunction with an actuator in a system commonly known as a metered dose inhaler (MDI) unit. The actuator includes a housing having one open end into which a canister is loaded and another open end serving as mouthpiece for the user. A nozzle element is disposed within the housing and includes a valve stem-receiving bore communicating with a nozzle orifice. The orifice is aimed toward the mouthpiece. In order to receive a properly metered dosage of medicine from the canister, the patient installs the canister into the actuator through the canister-loading end until the valve stem is fitted into the receiving bore of the nozzle element. With the canister so installed, the opposite end of the canister typically extends to some degree outside the actuator housing. The patient then places the mouthpiece into his or her mouth and pushes downwardly on the exposed canister end. This action causes the canister to displace downwardly with respect to the valve stem, which in turn unseats the valve. Owing to the design of the valve, the design of the nozzle element, and the pressure differential between the interior of the canister and the ambient air, a short burst of precisely metered, atomized medicine is thereby delivered to the patient.

As known to those skilled in the art, the quality of the manufacturing process of the MDI canister, especially the quality of the crimping process by which the valve cap is sealed onto the canister, is of utmost criticality. Even a slight defect in the resulting crimp will constitute an improperly sealed valve cap. That is, because of the significant pressure differential between the interior of the canister and the ambient air, the slightest leak will render the canister commercially and therapeutically valueless. By the time the defective canister has been distributed to the patient, most or all of the propellant will have escaped the confines of the canister. As a result, the pressure differential is eliminated and the canister rendered inoperative.

In addition, the magnitude of the force (or the range of magnitudes) exerted by the valve cap crimping tool typically utilized in MDI canister production lines is critical in ensuring an effective seal. In general, the act of adjusting the valve assembly crimping equipment on the production lines has been more art than science. As a result, the valve assembly crimping equipment can be improperly adjusted so that the frequency of canister and/or valve assembly defects has the potential to be unacceptably high. On the one hand, too much applied force might crush or otherwise deform the sealing edge of the can. On the other hand, too little applied force might produce a leaking valve and thus fail to create a good seal. Existing, conventional procedures entail a visual inspection of the crimp as well as crude measurements to ensure that the valve seal has been sufficiently compressed. The importance of proper calibration of the crimping equipment is hence well established among those skilled in the art.

One approach employed to verify the integrity of the valve seal has been to incorporate a quality-control mechanism such as a test firing station into the production line. After a canister has passed through the crimping station and a valve assembly has been installed onto the canister, the canister with its valve assembly is transported to a filling station at which a bulk quantity of medicament is conducted into the canister through the valve stem. Subsequently, the filled canister/valve assembly combination is transported to a test firing station. At the test firing station, an operative component bears down on the valve stem to mechanically actuate (or "fire") the valve assembly so that the operation of the valve assembly can be evaluated. As in the case of the upstream crimping equipment, importance of proper calibration of the test firing equipment is well recognized among those skilled in the art, and for similar reasons. That is, the magnitude of the actuating force imparted by the test firing equipment onto the valve assembly of the canister must fall within a certain accepted range of values. Otherwise, the test firing station may damage the valve assembly and/or the canister, or fail to properly actuate the valve and thus fail to enable a proper verification of manufacturing quality or actuating performance. Therefore, MDI canisters can be needlessly rejected if either too much or too little actuating force is applied at the test firing station.

It would therefore be advantageous to provide a feasible means for identifying and diagnosing problems associated with the manufacture of valve-equipped canisters, and with the assessment of performance of manufactured valve-equipped canisters. In particular, it would be advantageous to provide a feasible means for calibrating the crimping and test firing stations typically employed in MDI unit production lines. The present invention is provided to address these and other problems associated with the assembly of ends, tops or caps onto open-ended canisters, especially the installation of valve assemblies onto such canisters, as well as problems associated with the measurement of various axial forces imparted on canisters during manufacturing processes, such as crimping and actuating forces.

BRIEF DESCRIPTION OF THE DRAWINGS

FIG. 2 is a partially cutaway view of a metered dose inhaler unit consisting of an actuator operating in conjunction with the valve-equipped canister illustrated in FIG. 1A;

FIGS. 6A and 6B are top plan views of alternative forms of a top portion of the measuring device illustrated in FIGS. 3 and 4 in accordance with the present invention;

FIG. 7 is a side elevation view of the measuring device illustrated in FIGS. 3 and 4 with a valve assembly having been installed thereon in accordance with the present invention;

FIG. 8 is a diagram illustrating the measuring device of FIGS. 3 and 4 operating on an MDI production line in accordance with the present invention;

FIG. 15a is a perspective view of a battery charger for use in accordance with the present invention.

FIG. 15b is a diagram illustrating the battery charger set forth in FIG. 15a as assembled.

DETAILED DESCRIPTION OF THE INVENTION

Figure 1B:
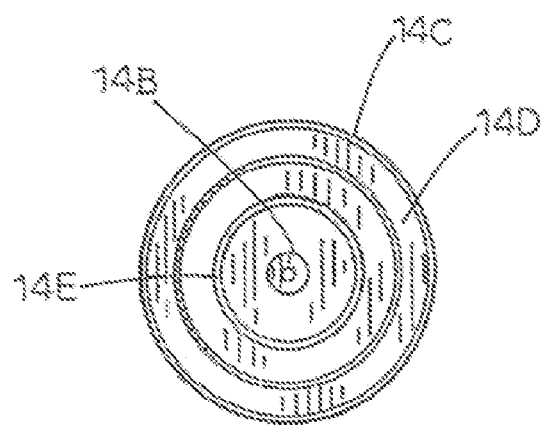
FIG. 1B is a top plan view of the canister illustrated in FIG. 1A.
Figure 1A:
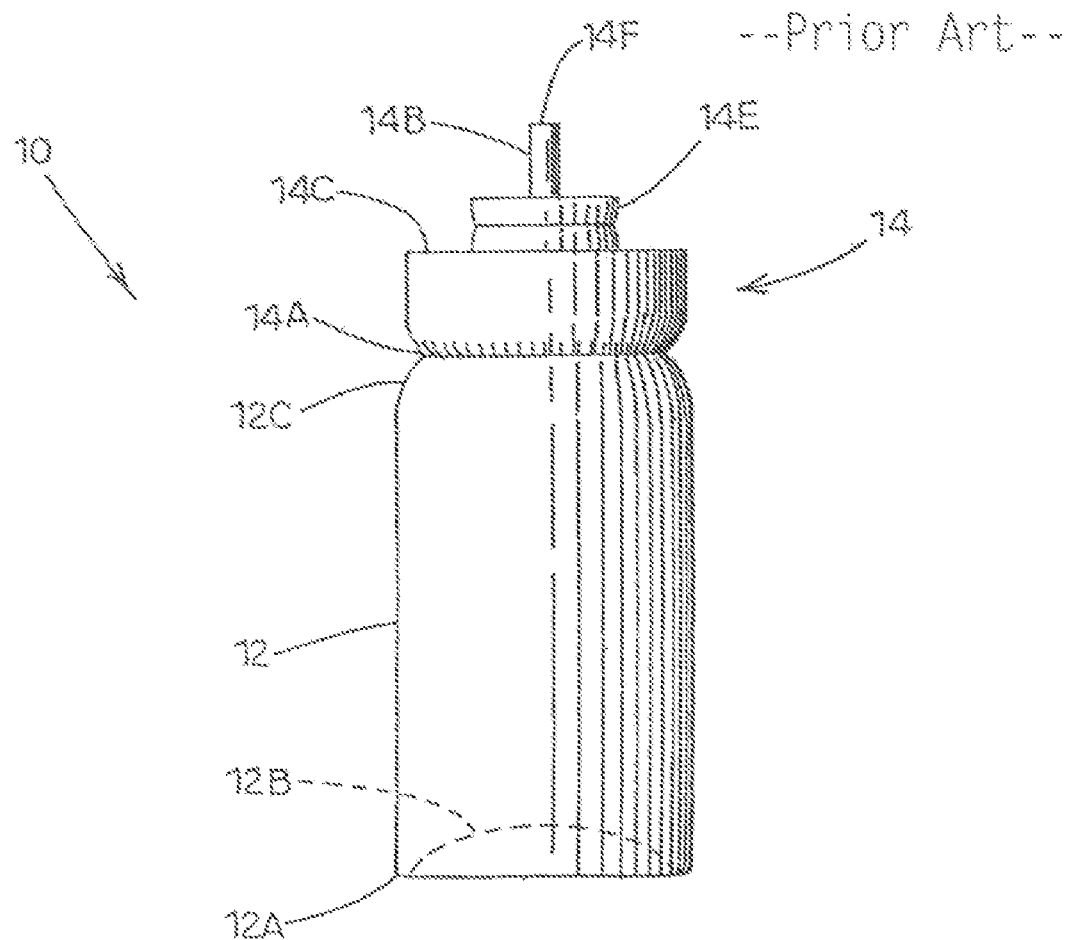
FIG. 1A is a side elevation view of a canister to be measured by a measuring apparatus provided in accordance with the present invention, with a valve assembly having been installed onto the canister.
Figure 1C:
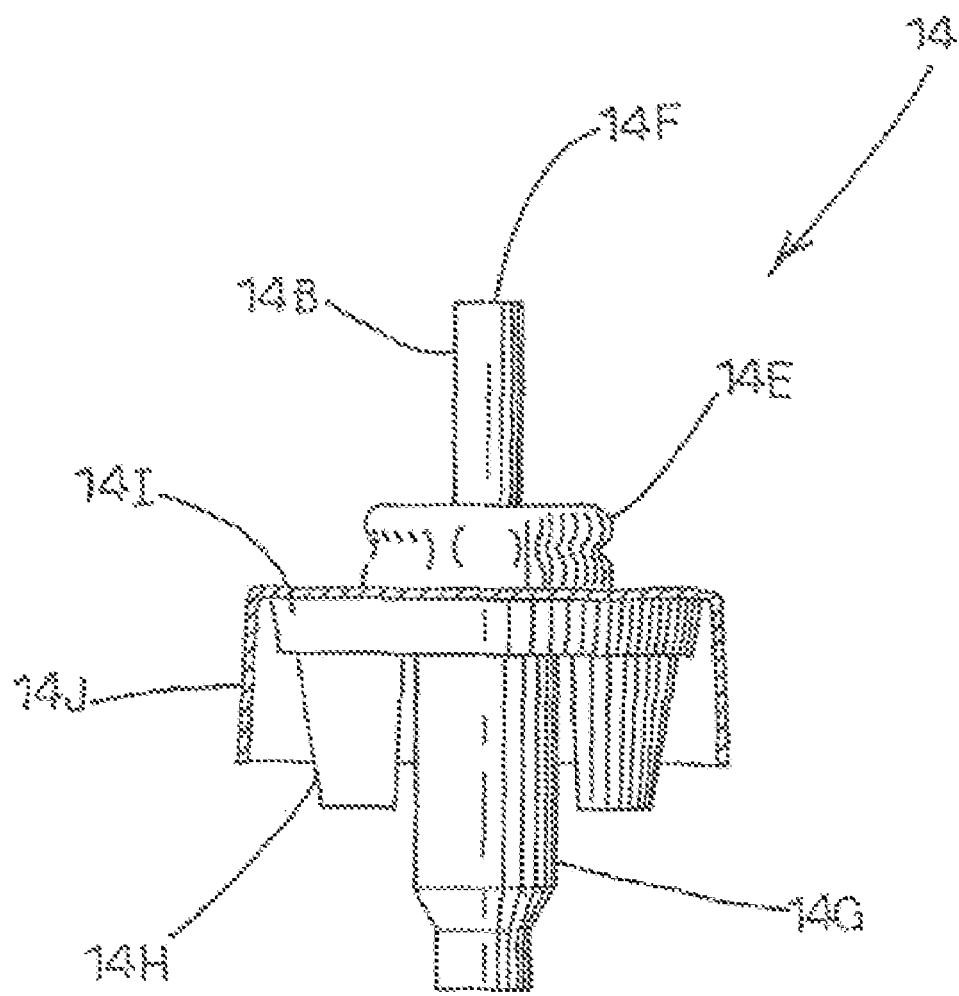
FIG. 1C is a partially cutaway view of the valve assembly illustrated in FIG. 1A.

Referring now to FIGS. 1A-1C, a typical MDI canister, generally designated 10, is illustrated. Canister 10 includes a canister body 12 having a typical diameter of 0.87 inches. There are typically three standard sizes for canister 10, which may be referred to as short, medium, and tall. Short, medium and tall canisters 10 typically have respective heights of 1.54, 1.93, and 2.37 inches. Short canister 10 typically delivers 60 or 80 metered doses, medium canister 10 typically delivers 120 doses, and tall canister 10 typically delivers 200 doses.

As shown in FIG. 1A, canister body 12 is bounded by a closed bottom canister end 12A, which usually has a concave profile 12B (shown in phantom), and an open upper canister end concealed by a valve assembly or cap, generally designated 14. A canister shoulder 12C provides a regional transition from canister body 12 to the upper canister end. Valve cap 14 is sealed over the upper canister end at a crimped section 14A. A hollow valve stem 14B extends outwardly from valve assembly 14. Valve assembly 14 includes contains a valve (not shown) communicating with the interior of canister body 12 in operative association with valve stem 14B. As shown in FIG. 1B, a top surface 14C of valve assembly 14 is flat in at least an annular region 14D of valve assembly 14. A raised top portion 14E of valve assembly 14 houses one or more gaskets (not shown) for sealing valve stem 14B as well as a metering chamber. The internally disposed end (not shown) of valve stem 14B fluidly communicates with the valve. The opposing, externally disposed end 14F of valve stem 14B serves as the dose delivery outlet. When valve stem 14B is depressed downwardly against the bias of its return spring, it momentarily opens the valve and thereby delivers a controlled, metered, atomized dose of medicament through valve stem 14B. The internal design and interaction of valve stem 14B, its return spring and the valve ensure that the valve is closed after the metered quantity of medicament is emitted through valve stem 14B, and also that the metered quantity is substantially consistent with repeated actuations of valve assembly 14.

Referring to the partially cutaway view of valve assembly 14 in FIG. 1C, the valve, the return spring and a portion of valve stem 14B are contained within an internal housing or valve body 14G of valve assembly 14. A resilient slotted ring 14H and a gasket 14I are also provided to ensure a good seal when valve assembly 14 is installed onto open-ended canister body 12. Additionally, valve assembly 14 includes a metallic outer skirt or ferrule 14J for use as the crimping material.

Referring to FIG. 2, a typical MDI unit, generally designated 20, is illustrated. Canister 10 with valve assembly 14 installed thereon has been loaded into an MDI actuator, generally designated 30. Actuator 30 includes a housing 32 having one open end 32A into which canister 10 has been loaded, and another open end 32B serving as the mouthpiece through which atomized medicament 34 is emitted from MDI unit 20. A nozzle element 36 is formed in housing 32. Nozzle element 36 includes a valve stem-receiving bore 36A fluidly communicating with a nozzle orifice 36B aimed toward the opening of mouthpiece 32B. MDI unit 20 is actuated by pressing down on exposed canister end 12A.

Figure 3:
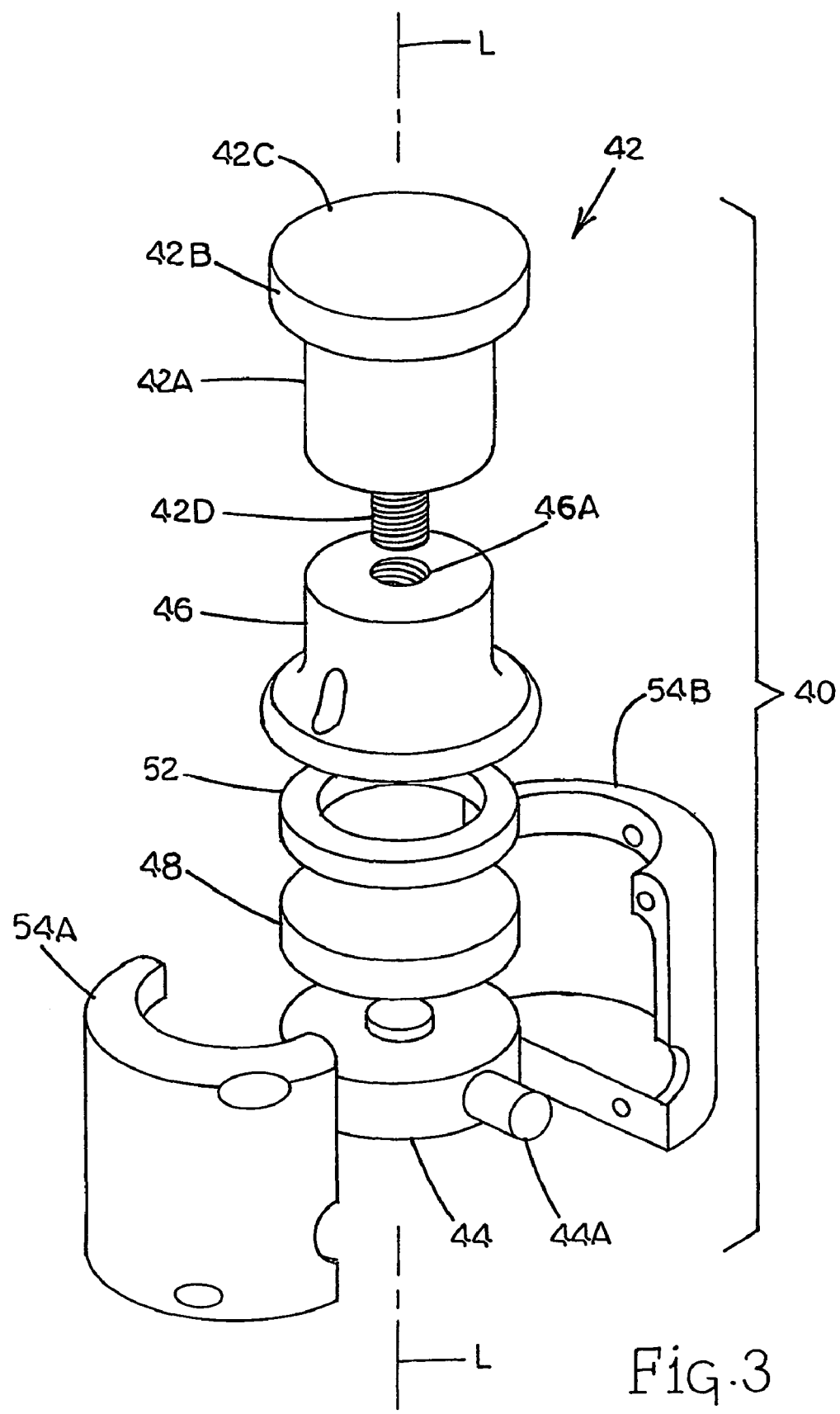
FIG. 3 is an exploded perspective view of an axial force measuring device according to one embodiment of the present invention.
Figure 4:
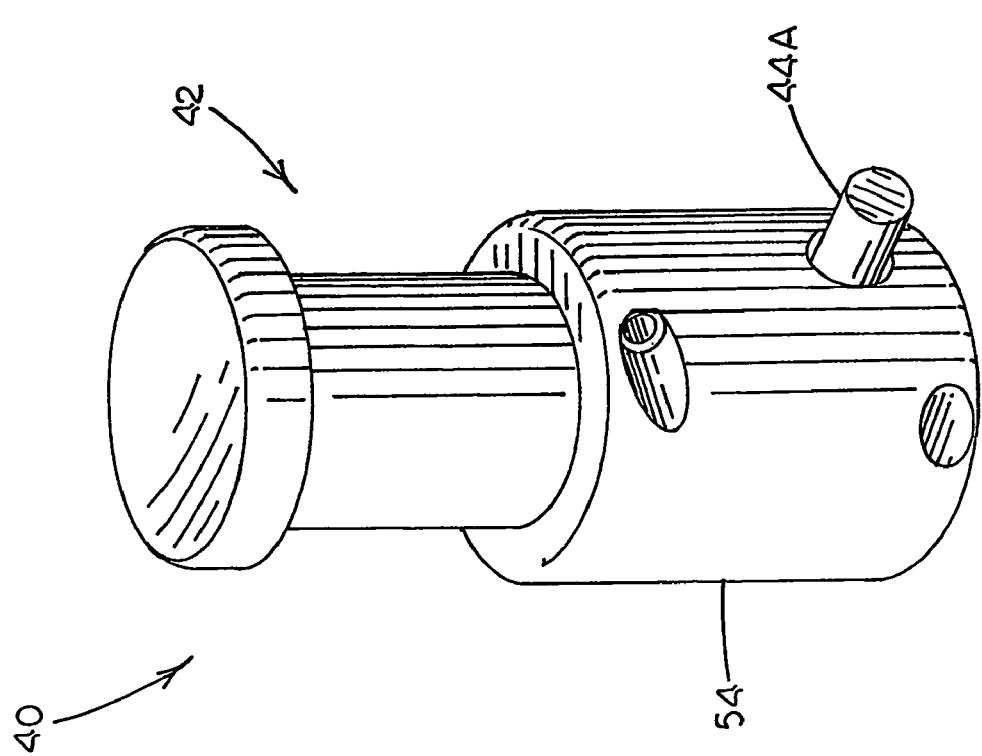
FIG. 4 is a perspective view of the measuring device illustrated in FIG. 3 in assembled form in accordance with the present invention.

Referring to the exploded and assembled views of FIGS. 3 and 4, respectively, one preferred embodiment of an axial force measurement device, generally designated 40, is illustrated in accordance with the present invention. This particular embodiment is most advantageously utilized as a crimp force measurement device. Preferably, the several components comprising device 40 are generally disposed along a longitudinal axis L of device 40. Primary operative components of device 40 include an interchangeable top or head member, generally designated 42, and a transducer 44 adapted to measure an axial force directed generally co-linearly or parallel with longitudinal axis L. Because head member 42 and transducer 44 are generally aligned along longitudinal axis L, any force (or at least the axial component of a resultant force) can be transferred from head member 42 to transducer 44. As understood by those skilled in the art, transducer 44 is designed to react to this force by producing an electrical signal proportional to the magnitude of the force picked up by transducer 44. For instance, the response of transducer 44 to an applied force can be a change in electrical resistance of an operative portion of transducer 44 that in turn results in a change in voltage output from transducer 44. A suitable transducer 44 is provided in the form of a load cell, such as that available from Transducer Techniques as Model No. 5LB-1K.

Head member 42 includes a main body 42A, a flanged portion 42B with a top impact surface 42C, and a mounting post 42D. Head member 44 is adapted for removable mounting to an adapter body 46. Preferably, mounting post 42D is threaded and a receiving bore 46A of adapter body 46 is likewise matingly threaded to enable head member 42 to be screwed into adapter body 46. Head member 42 can be provided with varying heights to enable device 40 to emulate the various standard sizes of typical MDI canisters 10, such as the short, medium and tall sizes described hereinabove. In this manner, and because head member 42 is interchangeable, device 40 can be adapted to emulate whatever size of canister 10 is being produced on a given production line.

Preferably, device 40 includes a distributor plate 48 to ensure that the force imparted on head member 42 is substantially uniformly distributed to transducer 44. Distributor plate 48 can be mounted to either primary surface of transducer 44. In the embodiment illustrated in FIGS. 3 and 4, distributor plate 48 is located on the side of transducer 44 facing head member 42. A cushion ring 52 is also provided between adapter body 46 and distributor plate 48 to improve the fit between adapter body 46 and distributor plate 48, but does not interfere with the measuring function of transducer 44. As also shown in FIGS. 3 and 4, device 40 includes an electrical connector 44A mounted to transducer 44 to enable signals generated by transducer 44 to be sent remotely from device 40. In addition, device 40 includes a housing 54 such as two shell halves 54A and 54B to protect transducer 44.

Figure 5:
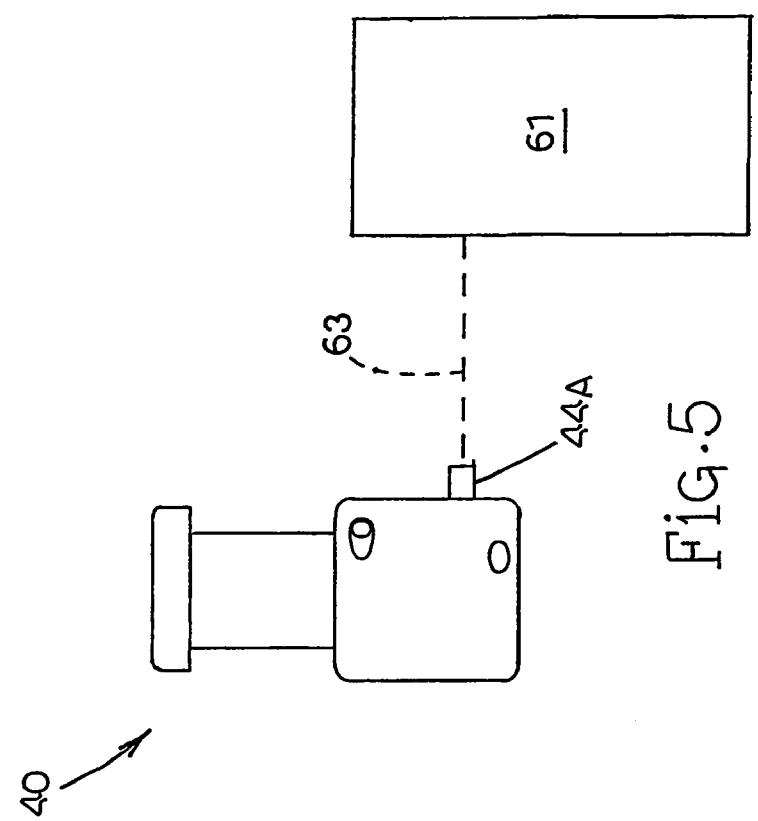
FIG. 5 is a diagram illustrating the measuring device of FIGS. 3 and 4 placed in operative communication with electronic circuitry in accordance with the present invention.

Referring to the diagram of FIG. 5, device 40 is adapted to communicate with appropriate electronic circuitry 61 through a suitable electrical conduit 63 connected to electrical connector 44A of transducer 44. As understood by those skilled in the art, electronic circuitry 61 can include the various components necessary for amplifying, conditioning, and storing signals produced by transducer 44. A display device (not shown) communicating with electronic circuitry 61 can also be provided to display a human-readable indication of the axial force measured by transducer 44.

In the embodiment shown in FIGS. 3 and 4, head member 42 (or at least its top surface 42C) is a solid piece, as further shown in the top view of FIG. 6A. Thus, device 40 can measure the axial force imparted by virtually any type of source. In the context of an MDI canister production line, described more fully hereinbelow, device 40 can be operatively positioned at a valve assembly crimping station in the place of an open-topped canister body such as canister body 12 illustrated in FIG. 1A. The crimping station is then operated without manipulating a valve assembly. That is, the operative crimping tool of the crimping station is made to bear down onto head member 42 in a manner normally occurring when the crimping tool seals a valve assembly, such as valve assembly 14 shown in FIGS. 1A-1C, onto open-topped canister body 12. Consequently, the downward axial force imparted by the crimping tool is translated to transducer 44, transducer 44 responds by producing a signal proportional to the amount of force encountered, and the signal is sent over electrical conduit 63 to electronic circuitry 61 (see FIG. 5) for processing, recording, and/or human-readable display. The information obtained through the operation of device 40 can be used by a production line operator to recalibrate crimping equipment either before or during a production run. For example, the information can be compared with data known or predetermined to be acceptable in order to assess whether the crimping station is applying too much or too little force during its operation.

Referring now to FIGS. 6B and 7, device 40 is illustrated in an alternative form. The primary difference between the embodiment illustrated in FIG. 6B and that illustrated in FIG. 6A is that head member 42 in FIG. 6B includes a hollow portion with a top opening 65 at its flanged portion 42B. With top opening 65 so provided, and due to the outer profile presented by head member 42 with its flanged portion 42B as shown in FIGS. 3-5, valve assembly 14 can be installed onto head member 42 by permitting the inner components of valve assembly 14 to enter the hollow region through top opening 65, and by crimping ferrule 14J of valve assembly 14 around the outer periphery of flanged portion 42B. Device 40 with valve assembly 14 so installed is shown in FIG. 7. The affixation of valve assembly 14 to device 40 is thus very similar to the actual sealing of valve assembly 14 onto canister body 12 as shown in FIG. 1A.

Referring to FIG. 8, a schematic diagram is illustrated of device 40 operating within the environment of an MDI canister production line. Generally, the production line includes some type of conveying device, generally designated 70, with a moving transport component 72 such as an endless belt or chain for transporting open-topped canisters 12 to a valve assembly crimping station, generally designated 75. According to various configurations and arrangements known to those skilled in the art, crimping station 75 includes some type of crimping tool 75A for crimping valve assemblies 14 in secured, sealed relation to each canister body 12 arriving at crimping station 75. In operation, crimping tool 75A exerts a downward axial force on each canister body 12 along the direction generally indicated by the arrow.

In FIG. 8, device 40 has been placed in operative alignment with crimping tool 75A. Accordingly, if device 40 is provided in the form wherein head member 42 is solid (see FIG. 6A), valve assembly 14 will not be operatively associated with crimping tool 75A. Instead, crimping station 75 is activated such that empty crimping tool 75A bears down onto top surface 42C of head member 42 (see FIG. 6A), the axial force transferred to device 40 from crimping tool 75A is read by transducer 44, and the output signal from transducer 44 is sent out to a remote location in the manner described hereinabove. If, however, device 40 is provided in the form wherein head member 42 is hollow (see FIG. 6B), valve assembly 14 is operatively handled by crimping tool 75A in the normal fashion. In this latter case, crimping station 75 is activated such that crimping tool 75A bears down onto head member 42 and affixes valve assembly 14 thereon as described previously. Again, the axial force transferred to device 40 from crimping tool 75A is read by transducer 44 and the output signal sent remotely in the manner described hereinabove. In the subsequent use of device 40, head member 42 containing valve assembly 14 can be used again by cutting valve assembly 14 off from head member 42, or can be replaced with a new head member 42.

Device 40 can be placed in operative position at crimping station from an offline location. This may require momentarily slowing down or even stopping the production line, especially if a valve assembly 14 is not to be installed onto device 40. It will be understood, however, that since device 40 is roughly the same size as canister body 12, it could be transported down the production line (at least that portion of the production line immediately upstream of crimping station 75) along with canister bodies 12, passed through crimping station 75, and then taken back off the production line. However, some accommodation would have to be provided to account for electrical conduit 63 connected to transducer 44.

Figure 9:
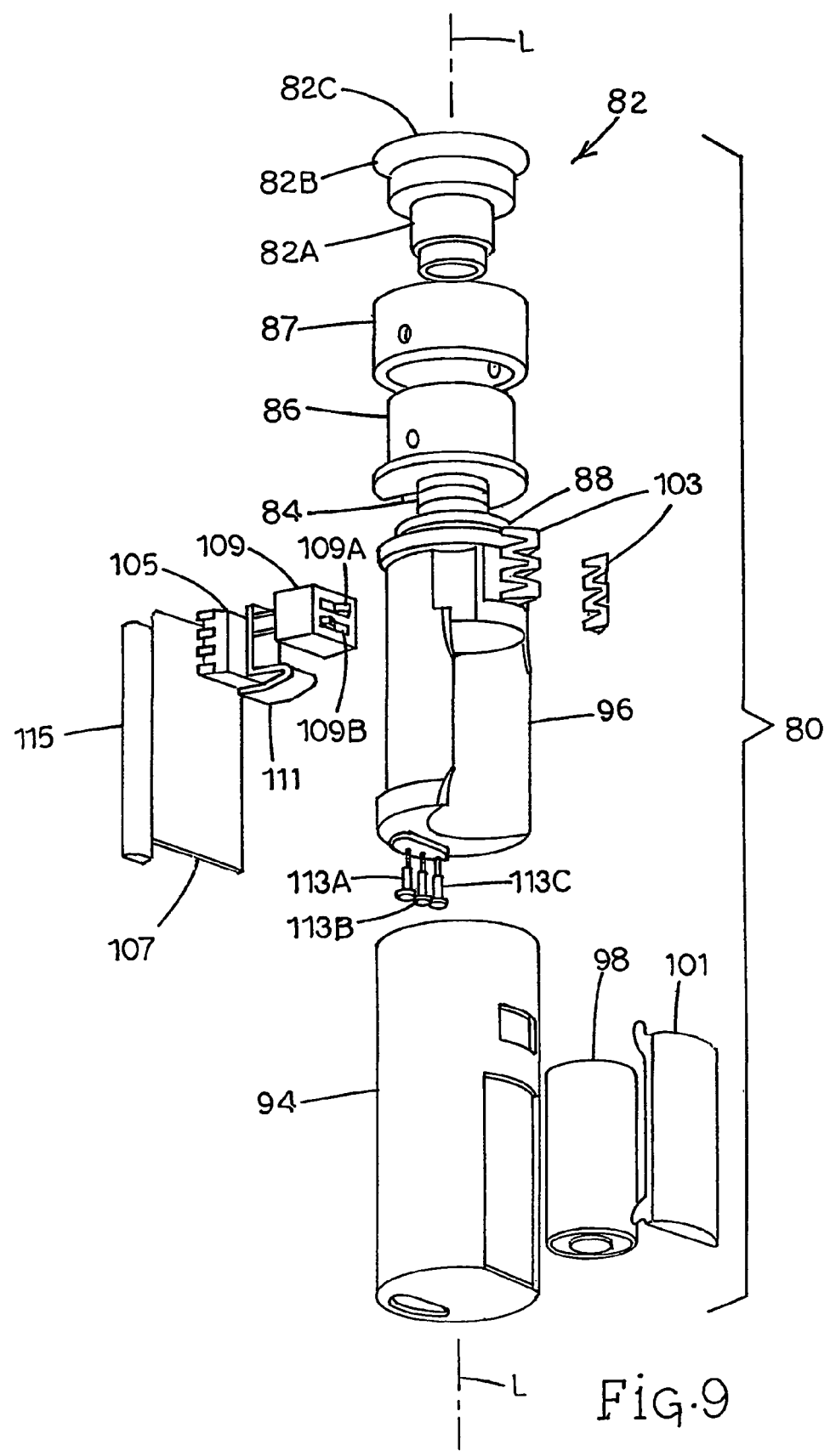
FIG. 9 is an exploded perspective view of an axial force measuring device according to another embodiment of the present invention.
Figure 10:
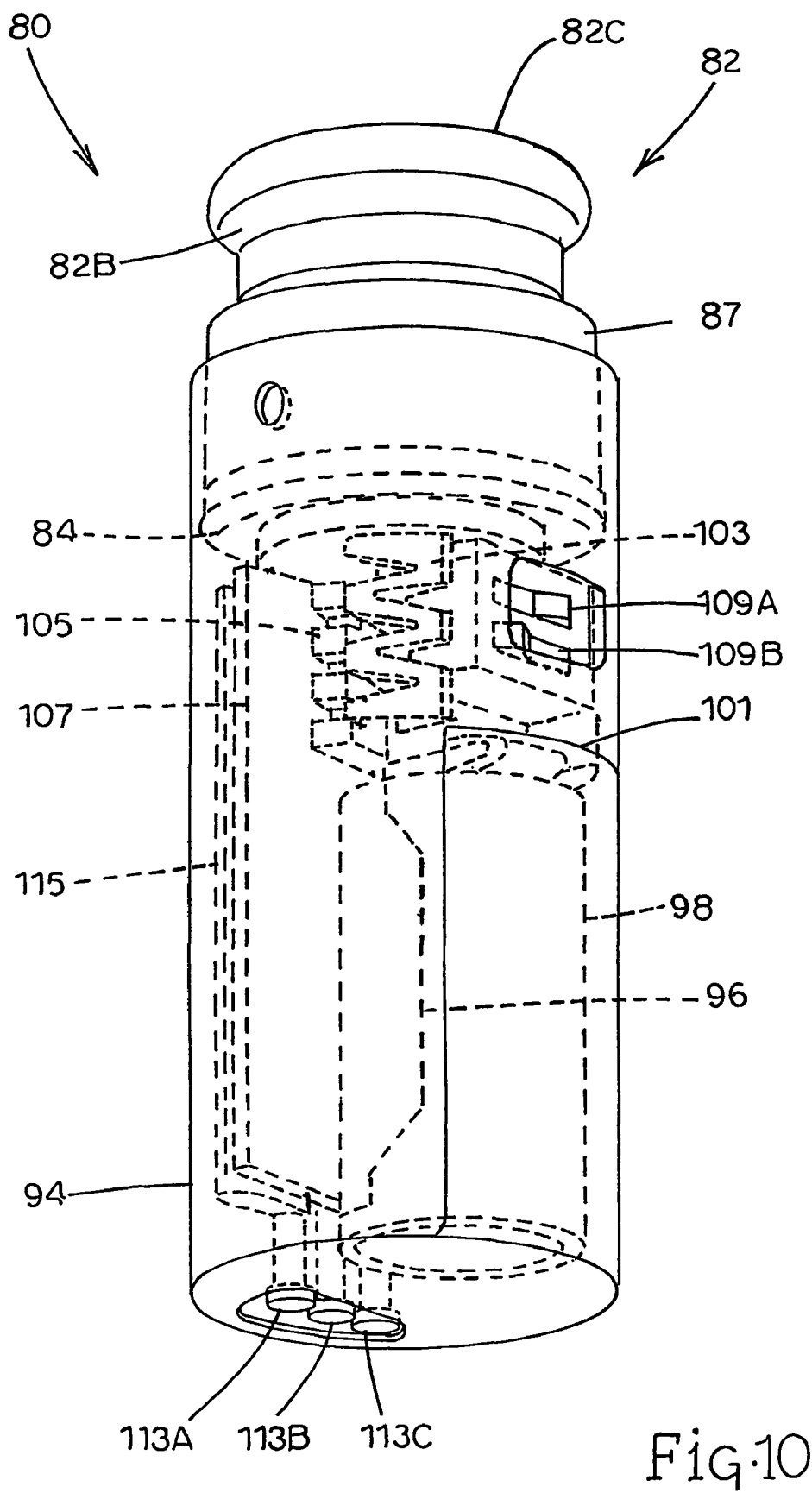
FIG. 10 is a perspective view of the measuring device illustrated in FIG. 9 in assembled form with interior parts illustrated in phantom line in accordance with the present invention.

Referring to the exploded and assembled views of FIGS. 9 and 10, respectively, another preferred embodiment of an axial force measurement device, generally designated 80, is illustrated in accordance with the present invention. This particular embodiment is most advantageously utilized as an actuating force measurement device although, as described further hereinbelow, may also be utilized as a crimp force measurement device. Similar to the previously described crimp force measurement device 40, the several components comprising device 80 are preferably generally disposed along a longitudinal axis L of device 80. Again, the primary operative components of device 80 include an interchangeable top or head member 82 and a transducer 84 adapted to measure an axial force directed generally co-linearly or parallel with longitudinal axis L. This arrangement enables force to be transferred from head member 82 to transducer 84. A suitable transducer 84 for this embodiment is provided in the form of a load cell, such as that available from Omega Engineering as Model No. LCKD-50.

Head member 82 includes a hollow main body 82A with a flanged portion 82B having an open top 82C, and thus is adapted to receive valve assembly 14. Head member 82 is removably inserted into an adapter body 86 and held in place with a retaining ring 87. Head member 82 can be provided with varying heights to enable device 80 to emulate the various standard sizes of typical MDI canisters 12 as described hereinabove. Device 80 is thus adaptable in a manner similar to device 40 described hereinabove with reference to FIGS. 3 and 4. Device 80 further includes a distributor plate 88 to ensure that the force imparted on head member 82 is substantially uniformly distributed to transducer 84. In the embodiment illustrated in FIGS. 9 and 10, distributor plate 88 is located on the side of transducer 84 facing head member 82, although distributor plate 88 could be mounted on the other side.

One primary difference between device 80 illustrated in FIGS. 9 and 10 and device 40 illustrated in FIGS. 3 and 4 is that device 80 is a self-contained unit in which both transducer 84 and data-related and power supply electrical components are integrated into device 80 and contained within a housing 94. It will thus be apparent that device 80 does not require a lengthy electrical conduit disposed externally with respect to housing 94.

In the specific example illustrated in FIGS. 9 and 10, device 80 includes a support block 96 to which an electrical power supply source in the form of a battery 98 is operatively mounted. Battery 98 is retained by a door 101 secured to support block 96 against one or more door springs 103. The various electronic circuitry components needed for amplifying, conditioning and storing output signals produced by transducer 84 are also contained within housing 94. Thus, device 80 includes an amplifier IC chip 105 and a data logger circuit board 107, as well as a power/mode switch box 109 in contact with a positive terminal plate 111. Switch box 109 includes an ON/OFF power switch 109A and a RECORD/COMMUNICATE switch 109B for switching device 80 between a RECORD mode and a COMMUNICATE mode, as described more fully hereinbelow. Preferably, three contact pads, 113A, 113B, and 113C, respectively, are provided for communication with an external data-related device if desired. Specifically, contact pads 113A-113C perform data transmit, data receive and handshaking functions, respectively, with housing 94 serving as the ground. Additionally, a temperature compensation board 115 includes electronic components such as a diode array to compensate for any effect that ambient temperature may have on the proper response of transducer 84. As understood by those skilled in the art, based on the ambient temperature at a given point in time during operation of device 80, temperature compensation board 115 offsets the actual reading given by transducer 84 so that the output signal stored or sent remotely is an accurate representation of the force measured by transducer 84.

Figure 11:
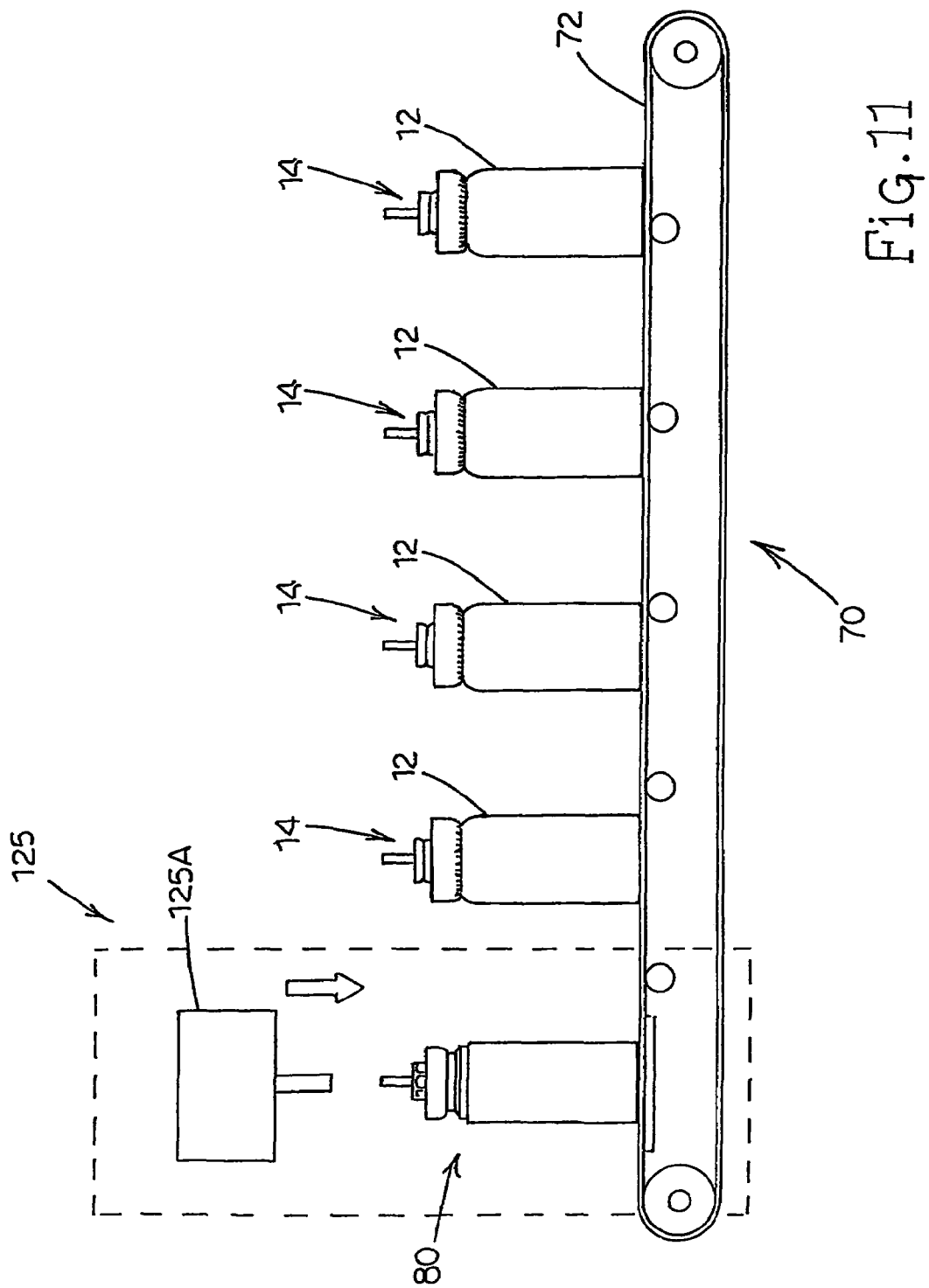
FIG. 11 is a diagram illustrating the measuring device of FIGS. 9 and 10 operating on an MDI production line in accordance with the present invention.

Referring to FIG. 11, a schematic diagram is illustrated of device 80 operating within the environment of an MDI canister production line including, for example, conveying device 70 with moving transport component 72 for transporting canisters 12 (with valve assemblies 14 sealed thereon by upstream crimping station 75, and with canisters 12 filled with medicament at a filling station) to a valve assembly test firing station, generally designated 125. According to various configurations and arrangements known to those skilled in the art, test firing station 125 includes some type of actuating tool 125A for bearing down on valve stem 14B of valve assembly 14 (see FIGS. 1A-1C). In operation, test firing tool 125A exerts a downward axial force on each valve assembly 14 along the direction generally indicated by the arrow.

Figure 12:
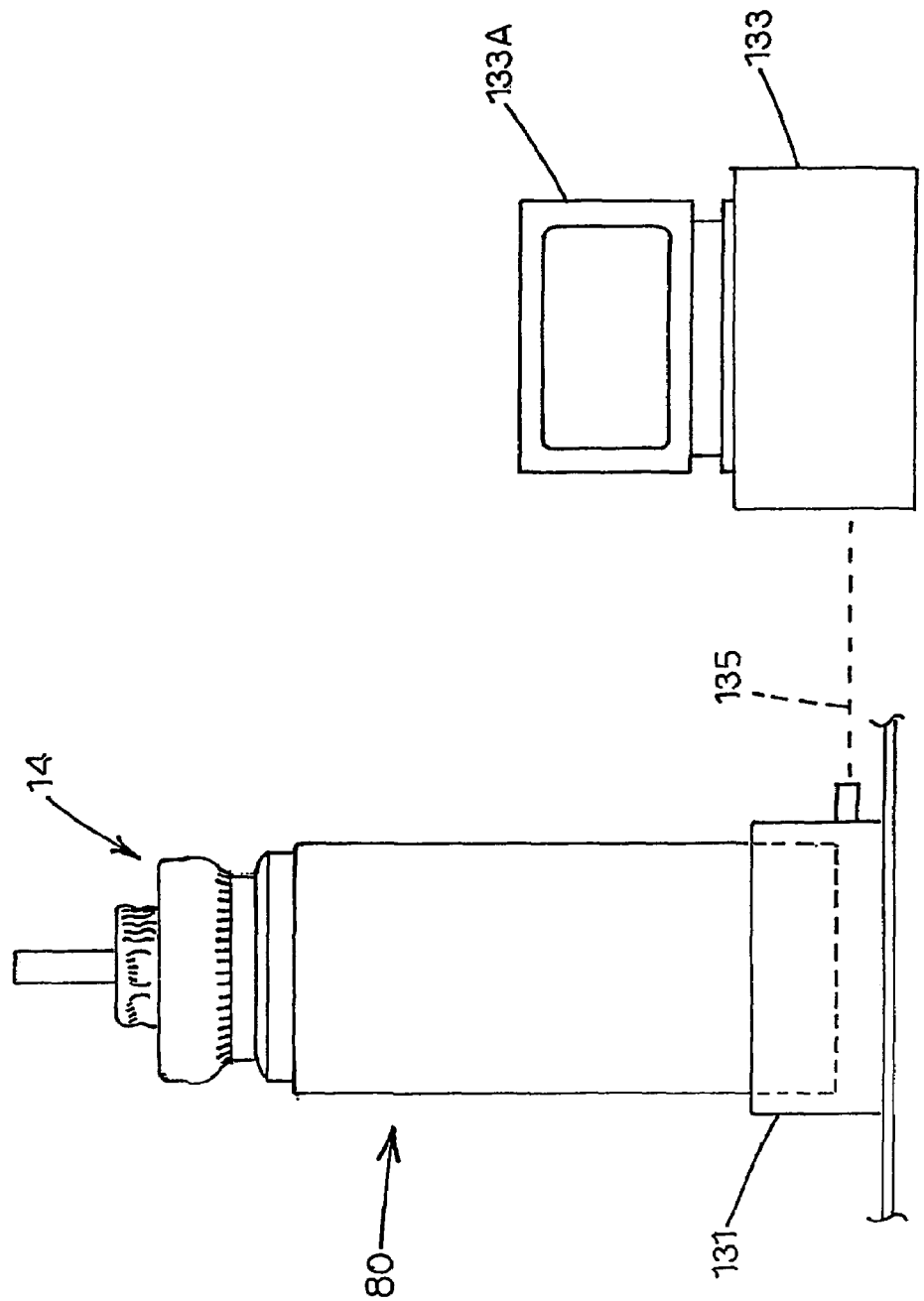
FIG. 12 is a diagram illustrating the measuring device of FIGS. 9 and 10 placed in operative communication with electronic circuitry in accordance with the present invention.

In FIG. 11, device 80 has been placed in operative alignment with actuating tool 125A. When RECORD/COMMUNICATE mode switching capability is provided as described previously, device 80 is first switched to RECORD mode to establish communication between transducer 84 and data logger 107. In another preliminary step, a valve assembly 14 is installed onto head member 82 by crimping ferrule 14J (see FIG. 1C) of valve assembly 14 around the outer periphery of flanged portion 82B of head member 82. This can be accomplished either through the use of a manual tool or by first passing device 80 through an automated crimping mechanism such as crimping station 75 illustrated in FIG. 8. Device 80 with valve assembly 14 so installed is shown in FIG. 12. As in the case of previously described device 40, the affixation of valve assembly 14 to device 80 is very similar to the actual sealing of valve assembly 14 onto canister body 12 as shown in FIG. 1A.

Because device 80 is a self-contained unit without an externally disposed electrical conduit, device 80 can be placed on transport component 72 upstream of test firing station 125 at some point after the filling station, and caused to pass through test firing station 125. When device 80 becomes operatively aligned with actuating tool 125A, test firing station 125 is activated such that actuating tool 125A bears down onto valve stem 14B and thereby actuates valve assembly 14 to release a metered dose of medicament. Because head member 82 is hollow, inner housing 14G (see FIG. 1C) of valve assembly 14 can actually contact transducer 84 upon actuation. Alternatively, axial force is translated through head member 82 and adapter body 86 to transducer 84. In either case, the axial force transferred to device 80 from test firing tool 125A is read by transducer 84 and the output signal is stored in data logger 107. In the subsequent use of device 80, head member 82 containing valve assembly 14 can be used again by cutting valve assembly 14 off from head member 82, or can be replaced with a new head member 82.

Device 80 is adapted for communication through its contact pads 113A-113C with external electronic data devices if desired. Accordingly, after device 80 has passed through test firing station 125 and has recorded axial force data, device 80 is removed from the production line and switched to the COMMUNICATE mode. Referring to FIG. 12, device 80 is preferably adapted to be mounting in a cradle 131 such that contact pads 113A-113C (see FIGS. 9 and 10) communicate with complementary contacts (not shown) of cradle 131. Cradle 131 communicates with a data processing device 133 such as a computer through an electrical conduit 135. Thus, in COMMUNICATE mode, communication is established between data logger 107 contained within device 80 and externally disposed computer 133 to enable transfer of data from device 80 to computer 133 for further data storage, interpretation and processing. Moreover, a display portion 133A of computer 133 can be used to display a human-readable indication of the axial force measured by transducer 84 at test firing station 125. The information obtained through the operation of device 80 can be used by a production line operator to recalibrate test firing equipment either before or during a production run. For example, the information can be compared with data known or predetermined to be acceptable in order to assess whether test firing station 125 is applying too much or too little force during its operation.

As an alternative embodiment, RECORD/COMMUNICATE switch 109B could be mounted in the base of cradle 131 instead of at switch box 109 on device 80. In this configuration, the mounting of device 80 into cradle 131 automatically switches device 80 to the COMMUNICATE mode, and the removal of device 80 from cradle 131 automatically switches device 80 to the RECORD mode. As a further alternative, a suitable electrical contact element can be added to cradle 131 to supply low voltage power to device 80 while device 80 is communicating through cradle 131, thereby conserving battery life. The modifications required to implement these alternative embodiments should be understood by persons skilled in the art. Such mod include the addition of one or more contact pads (which can be similar in form to contact pads 113A-113C) to the base of device 80.

It should be noted that device 80 can also serve as a crimp force measuring device in a manner analogous to device 40 as described hereinabove with reference to FIG. 8. In such a case, device 80 would need to be removed from the production line after being passed through crimping station 75, and subsequently placed back on the line before passing through test firing station 125. Device 80 must be first removed from the production line due to the intervening canister filling station. Accordingly, it is possible to utilize device 80 in the calibration of both crimping stations 75 and test firing stations 125.

Figure 13:
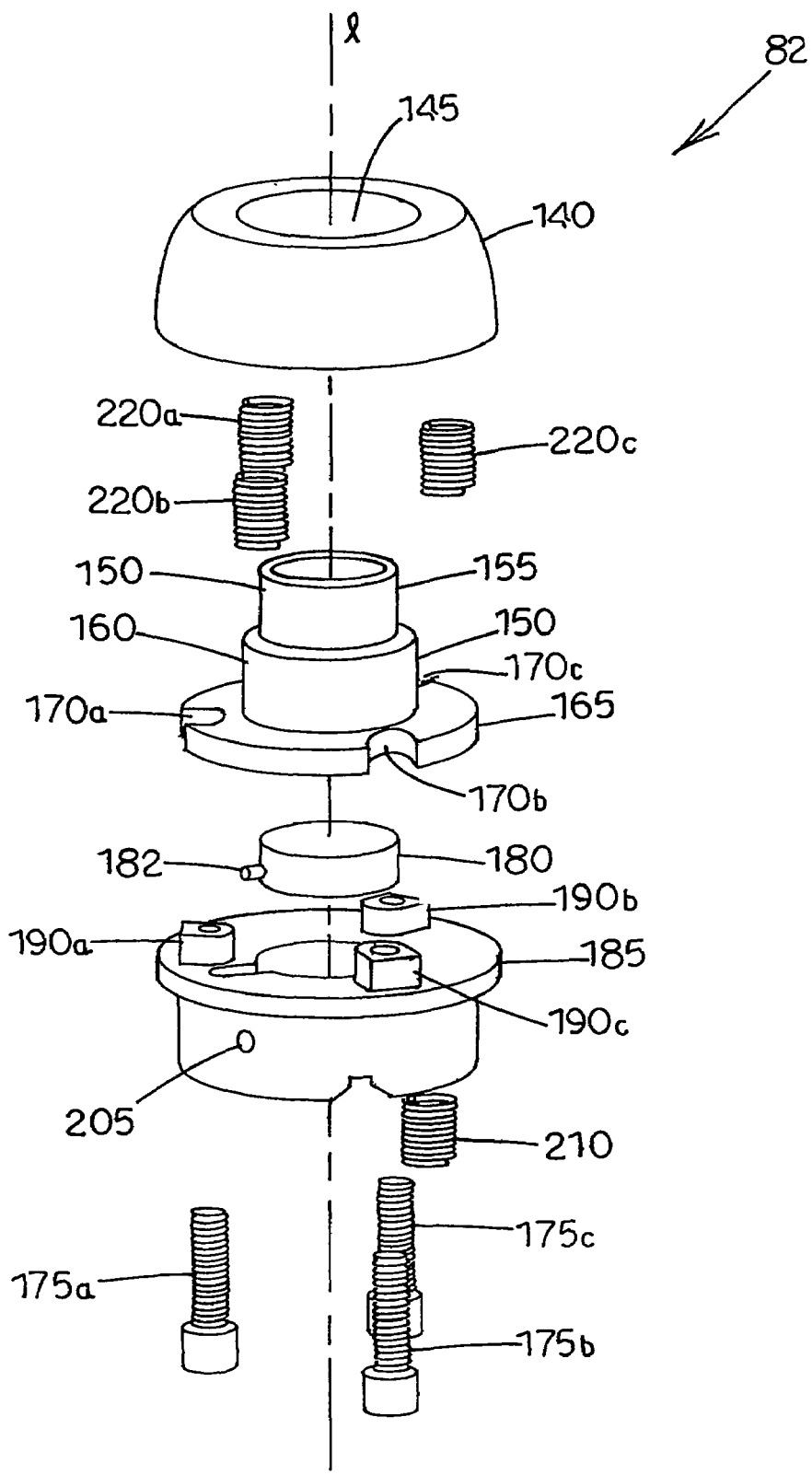
FIG. 13 is a perspective view of a head member for use with a measuring device in accordance with the present invention.

Another embodiment of head member 82 is set forth in FIG. 13. As illustrated therein, head member 82 includes a top neck plate 140 having a hollow portion 145 formed therein which is configured to receive a valve assembly including, without limitation, those described herein. As appreciated by one skilled in the art, hollow portion 145 may vary in size to accommodate the desires of the end user. Alternative to the embodiment in FIG. 13, the neck plate 140 may have a solid middle in place of hollow portion 145.

Beneath neck plate 140 is preload plate 150. As shown, preload plate 150 contains a top portion 155 which is configured in size to hollow portion 145 and mid portion 160 of greater diameter than top portion 155. Additionally, and as explained in greater detail herein, preload plate 150 includes a bottom flange portion 165 having a plurality of openings 170a, 170b, and 170c formed therein which are configured to receive fasteners 175a, 175b, and 175c.

Also shown in FIG. 13 is transducer 180. Similar to transducers described herein, transducer 180 responds to forces translated thereto by producing an electrical signal proportional to such forces. An opening 182 is formed in transducer 180 which permits electrical wires (not shown) to transmit electrical signals from the transducer to appropriate electrical circuitry. Transducer 180 is configured in size similar to mid portion 160 such that it may be received therein.

Head member 82 further includes bottom force plate 185. As depicted in FIG. 13, force plate 185 has an opening therein which is configured to receive transducer 180. Additionally, raised portions 190a, 190b, and 190c are present in force plate 185 and are designed to receive fasteners 175a, 175b, and 175c therethrough. Raised portions 190a, 190b, and 190c also correspond in size and shape to openings 170a, 170b, and 170c allowing fasteners 175a, 175b, and 175c to extend therethrough into the bottom portion of neck plate 140. An opening 205 is also present in force plate 190 and is capable of receiving electrical wires referred to hereinabove from transducer 180. Spring 210 is in contact with the bottom of force plate 190 and serves to contact a power source (e.g., battery) used in conjunction with head member 82.

Still referring to FIG. 13, fasteners 175a, 175b, and 175c extend through springs 220a, 220b, and 220c present in the lower portion 225 of neck plate 140. The presence of the springs 220a, 220b, and 220c in head member 82 is advantageous in that it is capable of allowing movement along the longitudinal axis of I member 82 when forces are imparted thereto while minimizing rotational movement.

Figure 14:
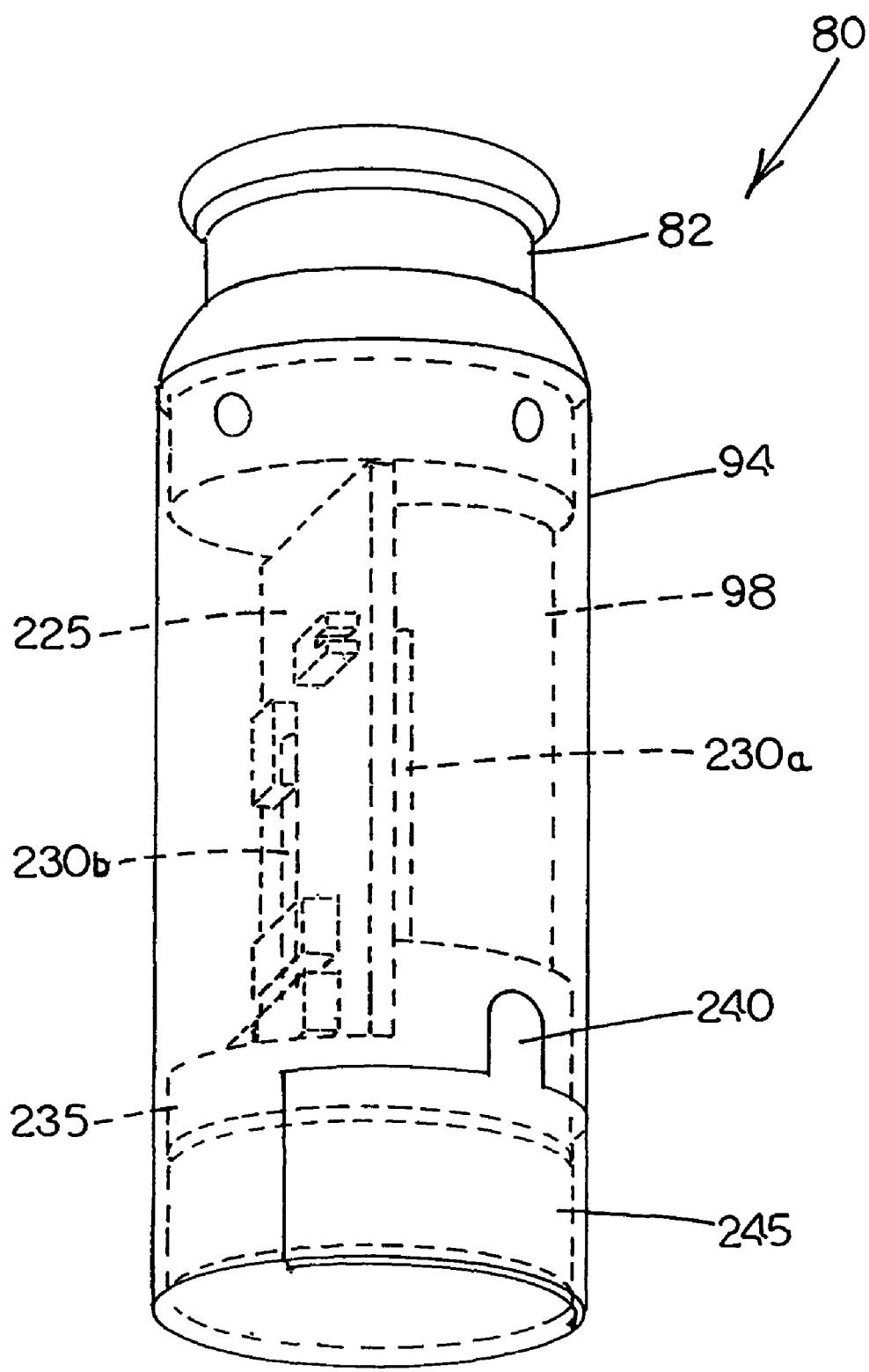
FIG. 14 is a diagram illustrating a measuring device in accordance with the present invention.

Another embodiment of device 80 is depicted in FIG. 14. It will be appreciated by one skilled in the art that the device 80 illustrated in FIG. 14 may be employed in combination with other various embodiments set forth herein. As an example, device 80 may be used in a canister production line such as that one illustrated in FIG. 11. In this specific embodiment, the head member 82 illustrated in FIG. 13 is employed; nonetheless, it will be appreciated that other head member embodiments described herein may be utilized in device 80 depicted by FIG. 14. In FIG. 14, battery 98 is present in the form of a rechargeable battery. As shown, a circuit card 225 is employed and is in communication with battery 98 as well as transducer 180 present in head member 82. A plurality of spring loaded probes 230a and 230b are present and are in communication with circuit card 225, as well as support plate 235 positioned in the bottom of housing 94. Such communication may be effected by various configurations. In one example, wires (not shown) may be employed to connect probes 230a and 230b to circuit card 225.

Still referring to FIG. 14, housing 94 has an opening 240 formed therein which is designed to receive and house data module 245. Data module 245 may be configured as necessary to have the capability to amplify, condition, and/or store signals produced by transducer 180. Transducer 180 communicates with data module 245 via probes 230a and 230b. As an example, one of the probes can assist in transmitting signals to and from transducer 180 and data module 245. Additionally, one of the probes assists in regulating the power available to data module 245.

The insertion of data module 245 in opening 240 and its contact with support plate 235 serves to power ON battery 98, thus allowing data module 245 to communicate with transducer 180. Upon completion of the force data gathering session, data module 245 may be removed from support plate 235 which serves to turn the battery 98 OFF. As desired by the end user, data module 245 may then be placed in communication with an additional electronic device(s) (not shown) for any number of operations such as, for example, data processing, storage, and/or display. As an example, data module 245 may be inserted in a computer.

As described hereinabove, battery 98 depicted in FIG. 14 is present as a rechargeable battery. Upon removal of data module 245, a charger may be inserted into opening 240 which functions to recharge battery 98. One example of a charger is set forth in FIGS. 15a and 15b, denoted as 255. As set forth in FIG. 15a, charger 255 includes a top plate 260 and a bottom plate 265. Top plate 260 has a peripheral wall 270 surrounding the plate so as to form opening 275 which is fitted to receive bottom plate 265. Spring loaded contacts 280 and 285 are configured to be received in top and bottom plates 260 and 265 respectively. Fastener 290 is also present and assists in maintaining the top and bottom plates in contact. In operation, charger 255 contacts with the positive terminal of battery 98 (not shown). Charger 255 also grounds against the bottom of housing 94. An embodiment of an assembled charger 255 is illustrated in FIG. 15b.

Figure 16:
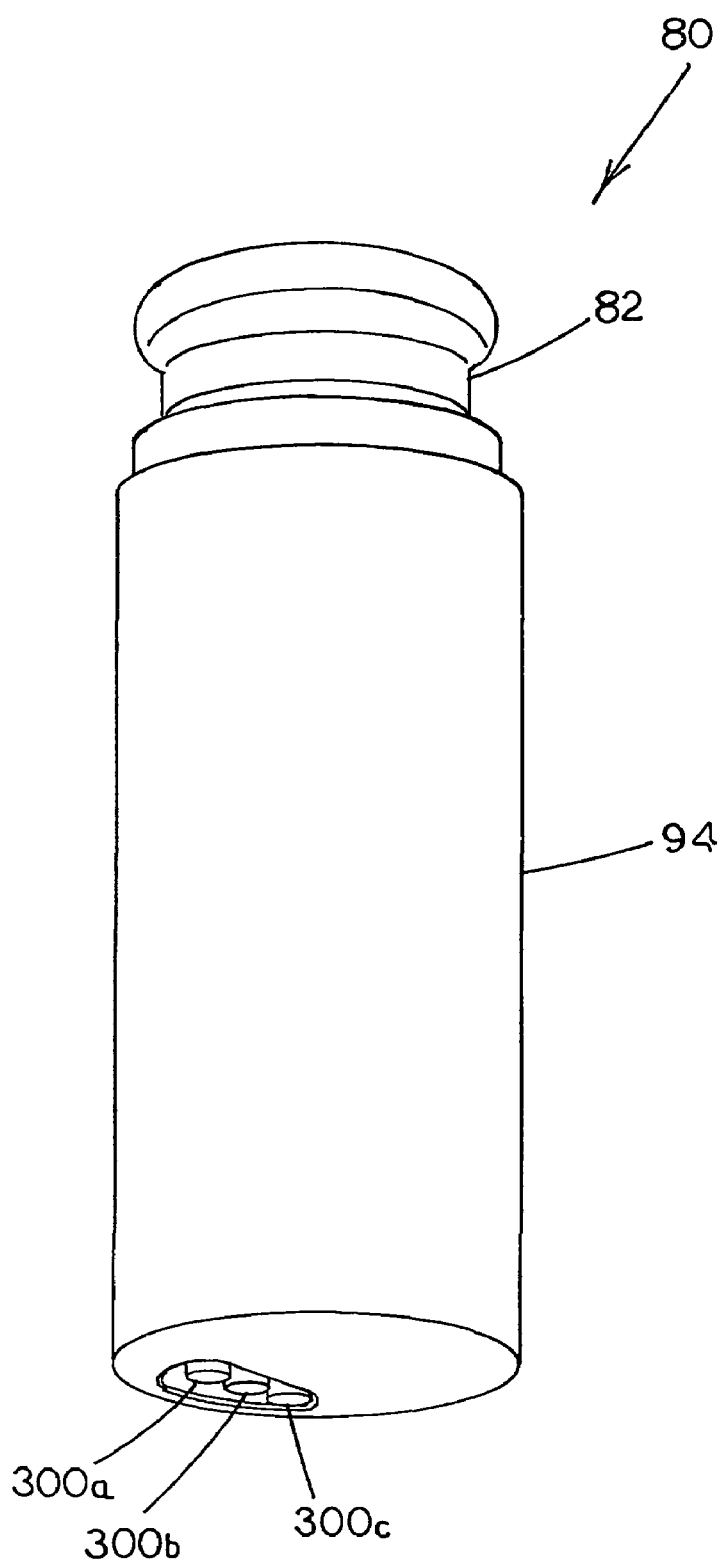
FIG. 16 is a diagram illustrating a measuring device in accordance with the present invention.

Another embodiment of device 80 is illustrated in FIG. 16. Such embodiment is similar to device 80 set forth in FIG. 14, except that housing 94 fully encloses data module 245, i.e., opening 240 is not present. Accordingly, device 80 further includes contact pads 300a, 300b, and 300c which are capable of serving as communication means for the various electronic components contained in device 80, e.g., transducer 180, data module 245, and/or battery 98, to external electrical circuitry. As an example, contact pads may assist in transmitting data from data module 245 for processing and/or reading of data stored therein. Moreover, in embodiments that employ battery 98 as a rechargeable battery, contact pads may assist in recharging battery 98 by communicating with an external power supply. As described with respect to the embodiment illustrated in FIG. 14, the insertion of data module 245 into device 80 serves to power ON the device. Since the data module 245 in FIG. 16 is enclosed, a switch may be employed in device 80 to regulate the power. The specific employment of such a switch embodiment may be carried out according to the desires of the end user.

It will be understood that various details of the invention may be changed without departing from the scope of the invention. Furthermore, the foregoing description is for the purpose of illustration only, and not for the purpose of limitation—the invention being defined by the claims.

What is claimed is:

1. An apparatus comprising:
   (a) a main body member;
   (b) a head member attached to the main body member, the head member including, an impact surface adapted for contact with a force; and
   a transducer in communication with the head member, the transducer adopted to receive force imparted to the head member
   wherein the head member includes a flanged portion extending radially outwardly from a longitudinal axis of the apparatus, the flanged portion includes an aperture coaxially disposed about the longitudinal axis, and the head member is adapted to receive a valve assembly secured around the flanged portion during a valve assembly crimping process.

2. An axial force measurement apparatus composing:
   (a) a head member coaxially disposed about a longitudinal axis of the measurement apparatus, the head member including a flanged portion extend radially outwardly from the longitudinal axis, wherein the head member presents an outer profile adapted to securably receive a value assembly on the head member during a valve assembly crimping process; and
   (b) an axial force transducer coaxially disposed about the longitudinal axis in mechanical communication with the head member, the transducer adapted to receive an axial force imparted to the head member generally along the longitudinal axis and transferred from the head member to the transducer, and adapted to produce an electrical output signal indicative of a magnitude of the axial force transferred to the transducer.

3. The apparatus according to claim 2 comprising electronic circuitry communicating with the transducer and adapted to receive the output signal produced by the transducer.

4. The apparatus according to claim 3 wherein the electronic circuitry is disposed remotely in relation to a housing of the apparatus and communicates with the transducer through an electrical conduit.

5. The apparatus according to claim 3 wherein the electronic circuitry is disposed within a housing of the apparatus.

6. The apparatus according to claim 5, wherein the electronic circuitry is present in a data module, and wherein said data module is capable of processing the output signal produced by the transducer.

7. The apparatus according to claim 6, wherein the data module is removable from the apparatus.

8. The apparatus according to claim 5 comprising at least one electrical contact accessible from outside the housing and adapted to enable communication between the electronic circuitry and an external computer device disposed remotely in relation to the housing.

9. The apparatus according to claim 8 comprising a mode switch electrically communicating with the electronic circuitry and accessible from outside the housing, the mode switch being alternatively switchable to a record mode of the apparatus and to a communicate mode of the apparatus, wherein electrical communication is established between the transducer and the electronic circuitry in the record mode, and electrical communication is established between the electronic circuitry and the external computer device in the communicate mode.

10. The anparatus according to claim 9 wherein the mode switch is mounted to the apparatus.

11. The apparatus according to claim 9 comprising a cradle in which the apparatus is adapted to be mounted, the cradle including tho mode switch.

12. The apparatus according to claim 11 wherein the cradle includes a contact adapted for electrical communication with the apparatus to provide power to the apparatus.

13. An axial force measurement apparatus comprising:
(a) a head member coaxially disposed about a longitudinal axis of the measurement apparatus, the head member including a flanged portion extending racially outwardly from the longitudinal axis, wherein the head member presents an outer profile adapted to securably receive a valve assembly on the head member during a valve assembly crimping process;
(b) an axial force transducer coaxially disposed about the longitudinal axis in mechanical communication with the head member, the transducer adapted to receive an axial force imparted to the head member generally along the longitudinal axis and transferred from the head member to the transducer, and adapted to produce an electrical output signal indicative of a magnitude of the axial force transferred to the transducer; and
(c) electronic circuitry disposed remotely in relation to the transducer and communicating with the transducer through an electrical conduit, the electronic circuitry adapted to receive the output signal produced by the transducer.

14. An axial force measurement apparatus comprising:
(a) a head member coaxially disposed out about a longitudinal axis of the measurement apparatus, the head member including a flanged porting extending radially outward from the longitudinal axis, wherein the head member presents an outer profile adapted to securably receive a valve assembly on the head member during a valve assembly crimping process;
(b) a housing;
(c) an axial force transducer disposed within the housing in mechanical communication with the head member, the transducer adapted to receive an axial force imparted to the head member generally along the longitudinal axis and transferred from the head member to the transducer, and adapted to produce an electrical output signal indicative of a magnitude of the axial force transferred to the transducer; and
(d) electronic circuitry disposed within the housing in communication with the transducer and adapted to receive the output signal produced by the transducer.

15. A method for measuring the axial force applied by a machine element, comprising the steps of:
(a) providing an axial force measurement apparatus including a head member coaxially disposed about a longitudinal axis of the measurement apparatus and an axial force transducer mechanically communication with the head member;
(b) causing a machine element to apply a force having an axially-oriented force component to the head member, wherein the axially-oriented force component is translated from the head member to the transducer; and
(c) using the transducer to produce an electrical output signal indicative of the axially-oriented force component translated to the transducer during application of the force to the head member.

16. The method according to claim 15 comprising the step of installing a valve assembly onto the head member by crimping the valve assembly around an outer periphery of the head manner.

17. The method according claim 15 comprising the step of operatively aligning the measurement apparatus at a valve assembly crimping station, wherein the machine element is a crimping tool.

18. The method according to claim 15 comprising the step of operatively aligning the measurement apparatus at a metered dose inhaler canister test firing station, wherein the machine element is a valve actuation tool.

19. The method according to claim 15 comprising the step of storing the signal produced by the transducer in a digital data format in an electronic data storage medium disposed externally in relation to the measurement device.

20. The method according to claim 15 comprising the step of storing the signal produced by the transducer in a digital data format in an electronic data storage medium housed within the measurement device.

21. The method according to claim 15 comprising the step of storing the signal produced by the transducer in digital data format in an electronic storage medium disposed internally in the measurement device.

22. The method according to claim 21 wherein the electronic storage medium is present as a data module, and wherein the data module is removable from the measurement device.

23. The method according to claim 15 comprising the steps of switching the measurement device to a record mode to store the signal produced by the transducer in a digital data format, and subsequently switching the measurement device to a communicate mode to send it stored digital data to a computer device.

24. A system for determining whether a valve assembly crimping station, as utilized on a metered dose inhaler unit production line, is properly calibrated, the system comprising:
(a) a valve assembly crimping station; and
(b) an axial force measurement device adapted for operative alignment with the crimping station, the measurement device including:

(i) a head member coaxially disposed about a longitudinal axis of the measurement apparatus, the head member including a flanged portion extending radially outwardly from the longitudinal axis, wherein the head member presents an outer profile adapted to securably receive a valve assembly on the head member during a valve assembly crimping process effected at the crimping station;

(ii) an axial force transducer coaxially disposed about the longitudinal axis in mechanical communication with the head member, the transducer adapted to receive an axial force imparted to the head member by the crimping station generally along the longitudinal axis and transferred from the head member to the transducer, and adapted to produce an electrical output signal indicative of a magnitude of the axial force transferred to the transducer; and (iii) electronic circuitry communicating with the transducer and adapted to receive the output signal produced by the transducer.

25. The system according to claim 24 comprising a conveying assembly including a movable transport device directed to and from the comprising station, wherein the measurement device is disposed on the transport device and moves with the transport device.

26. A system for determining whether a metered dose delivery device test firing station, as utilized on a metered dose inhaler unit production line, is properly calibrated, the system comprising:

(a) a test firing station adapted to actuate a valve assembly; and (b) an axial force measurement device adapted for operative alignment with the test firing, station, the measurement device inducting:

(i) a head member coaxially disposed about a longitudinal axis of the measurement apparatus, the head member including a flanged portion extending radially outwardly from the longitudinal axis, wherein the head member presents an outer profile adapted to securably receive a valve assembly on the head member during a valve assembly crimping process;

(ii) a valve assembly installed on the head member around the outer profile, the valve assembly including a valve and a valve stem in actuatable engagement with the valve;

(iii) an axial force transducer coaxially disposed about the longitudinal axis in mechanical communication with the head member, the transducer adapted to receive an axial force imparted to the valve assembly by the test firing station generally along the longitudinal axis and transferred from the valve assembly, through the head member and to the transducer, and adapted to produce an electrical output signal indicative of a magnitude of the axial force transferred to the transducer; and (iv) electronic circuitry communicating with the transducer and adapted to receive the output signal produced by the transducer.

27. The system according to claim 26 comprising a conveying assembly including a movable transport device directed to and from the test firing station, wherein the measurement device is disposed on the transport device and moves with the transport device.

* * * * *